United States Patent
Pollmeier et al.

(10) Patent No.: US 9,585,871 B2
(45) Date of Patent: Mar. 7, 2017

(54) METHOD FOR TREATING AND CURING LEISHMANIOSIS USING FEXINIDAZOLE

(71) Applicant: Merial Limited, Duluth, GA (US)

(72) Inventors: Matthias Pollmeier, Francheville (FR); Jeffrey Lynn Blair, Lyons (FR)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 14/169,713

(22) Filed: Jan. 31, 2014

(65) Prior Publication Data
US 2014/0213624 A1 Jul. 31, 2014

Related U.S. Application Data

(60) Provisional application No. 61/758,918, filed on Jan. 31, 2013.

(51) Int. Cl.
*A61K 31/4164* (2006.01)

(52) U.S. Cl.
CPC ................ *A61K 31/4164* (2013.01)

(58) Field of Classification Search
None
See application file for complete search history.

(56) References Cited

U.S. PATENT DOCUMENTS

2009/0042978 A1  2/2009  Castanedo Cancio et al.

FOREIGN PATENT DOCUMENTS

WO   WO 2008/007262 A2   1/2008

OTHER PUBLICATIONS

Wyllie, S. et al., The Anti-Trypanosome Drug Fexinidazole Shows Potential for Treating Visceral Leishmaniasis, Feb. 2012, Science Translational Medicine, vol. 4, Iss. 119, 119re1, pp. 1-7.*
Wyllie S. et al. "Assessing the essentiality of *Leishmania donovani* nitroreductase and its role in nitro drug activation", Antimicrobial Agents and Chemotherapy, vol. 57, No. 2, Dec. 3, 2012 (Dec. 3, 2012). pp. 901-906.
Els Torreele et al. "Fexinidazo le—A New Oral Nitroimidazole Drug Candidate Entering Clinical Development for the Treatment of Sleeping Sickness", PLOS Neglected Tropical Diseases, vol. 4, No. 12, Dec. 21, 2010 (Dec. 21, 2010), p. e923.
Grosjean. JAVMA, Views: Letters to the Editor. vol. 222, No. 10, May 15, 2003.
Haldar AK. Use of Antimony in the Treatment of Leishmaniasis: Current Status and Future Directions. Molecular Biology International. vol. 2011, Article ID 571242, 23 pages.
Martínez-Subiela. Serum concentrations of acute phase proteins in dogs with leishmaniasis. Vet. Record. 2002. vol. 150 pp. 241-244.
Wyllie S. The Anti-Trypanosome Drug Fexinidazole Shows Potential for Treating Visceral Leishmaniasis. Sci. Tran. Med. Feb. 1, 2012 vol. 4 Issue 119.

* cited by examiner

*Primary Examiner* — Kortney L Klinkel
*Assistant Examiner* — Tori M Strong
(74) *Attorney, Agent, or Firm* — Judy Jarecki-Black; Chad Kitchen; Merial, Inc.

(57) ABSTRACT

The present invention encompasses methods of using fexinidazole to treat and eliminate and/or cure *L. infantum* infections in canines.

13 Claims, No Drawings

METHOD FOR TREATING AND CURING LEISHMANIOSIS USING FEXINIDAZOLE

INCORPORATION BY REFERENCE

This application claims priority to provisional application U.S. Ser. No. 61/758,918, filed on Jan. 31, 2013, which is incorporated by reference herein in its entirety. All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to formulations for combating *Leishmania* infections in animals. Specifically, the present invention provides pharmaceutical compositions of fexinidazole and methods of treating, controlling, and completely eradicating or curing leishmaniosis.

BACKGROUND OF THE INVENTION

*Leishmania* is a genus of Trypanosomatid protozoa, and is the parasite responsible for the disease leishmaniosis which is a major and severe parasitic disease that affects humans, canines, and to a lesser degree, felines. *Leishmania* species are spread through sandflies of the genus *Phlebotomus* in the Old World and of the genus *Lutzomyia* in the New World. In humans, there are several forms of the disease named by their clinical presentation including cutaneous, mucocutaneous or visceral leishmaniosis caused by a variety of species of *Leishmania*. The predominant cause of canine leishmaniosis is *L. infantum* (sometimes referred to as *L. chagasi* in New World) which causes both visceral and cutaneous forms in dogs and the clinical distinction of the form of disease is less important. *L. infantum* is a cause for all forms of disease in humans and dogs serve as the primary reservoir for human infections caused by this species (Baneth G et al). *L. infantum* is widely distributed in temperate and subtropical countries of Southern Europe, Africa, Asia, South America and Central America, and the incidence of *L. infantum* is expanding geographically (Dantas-Torres F et al., 2012, Baneth G et al., Peterson CA et a/.2009, Ready PD et al., Miro G et al. 2010).

Canine leishmaniosis is a slowly progressive disease that can take years to become clinically apparent (McConkey S E et al., 2002). Signs are frequently non-specific and diagnosis in non-endemic regions is often overlooked. Some dogs appear naturally resistant to this parasite and can act as asymptomatic reservoir hosts (Grosjean N L et al., 2003). Approximately 10% of dogs residing in endemic areas actually develop clinical disease (Lindsay D S et al., 2002). Some of the more frequently reported clinical signs of leishmaniosis include skin lesions, listlessness, fatigue and exercise intolerance coupled with anorexia and weight loss that eventually culminate as wasting disease with chronic renal failure as the main cause of mortality (McConkey S E et al.; Solano-Gallego L et al). These signs may or may not be accompanied by fever, local or generalized lymphadenopathy, and hepatosplenomegaly (Grosjean N L et al., 2003; Lindsay D S et al., McConkey S E et al.; Martinez-Subiela S et al., 2002). Articular involvement is also fairly common and may present as lameness with swollen joints or simply as a stiff gait. Less common findings include ocular lesions (<5%), chronic diarrhea (30%) and long, deformed brittle nails (20%) referred to as onychogryphosis (Lindsay D S et al., Slappendel R J et al.).

Currently there are three drugs specifically approved for the treatment of canine leishmaniosis in Europe: N-methylglucamine (meglumine) antimoniate (GLUCANTIME®, Merial), miltefosine (MILTEFORAN®, Virbac), and domperidone (LEISHGUARD®, Esteve, Spain). The most commonly recommended treatment protocols for dogs with clinical leishmaniosis by European veterinary groups are meglumine antimoniate or miltefosine in combination with allopurinol, a xanthine oxidase inhibitor with anti-*leishmania* properties (Oliva G et al., Solano-Gallego L et al.). Domperidone is an antidopaminergic compound that has been demonstrated to enhance the cell mediated immune response to *leishmania* infection in dogs. Even in combination with allopurinol, both meglumine antimoniate and miltefosine do not result in a parasitologic cure 100% of the time, and relapse of disease is common (Mana L et al., Mateo M. et al., Solano-Gallego L et al., Oliva G et al.) Domperidone is indicated for the prevention or treatment of mild to moderate cases of canine leishmaniosis and its use in combination therapies is under investigation (Solano-Gallego L et al.). In addition to the inability to produce a parasitologic cure, all of the recommended treatment protocols are associated with significant side effects: meglumine antimoniate is associated with nephrotoxicity and cellulitis at the injection site, miltefosine is associated with vomiting and diarrhea, and allopurinol can induce xanthine urolithiasis (Solano-Gallego L et al.).

Mass detection of seropositive dogs followed by culling and/or drug treatment or the mass application of deltamethrin-impregnated collars were shown to have an impact in reducing human and canine leishmaniosis prevalence in endemic areas of Southern Europe, Africa, and Asia (Maroli et al., 2001; Mazloumi Gavgani A. S. et al., 2002), although the efficacy of eliminating seropositive canines has been debated (Dietze R et al., 1997; Moreira Jr. et al., 2004). These control measures are either considered unacceptable, expensive or not effective (Gradoni L. et al., 2005). Encouragingly, Susan Wyllie (Sci Transl. Med 4, 119, 2012) recently reported fexinidazole was able to suppress infection due to *L. donovani* infection (*leishmania* species affecting humans). However, it is not known whether the drug will work against the predominantly canine *leishmania* strain, *L. infantum*, nor is it known whether complete elimination (also referred to herein as "curing") of canine leishmaniosis infection is possible. "Elimination" or "curing" is deemed to be "substantially complete" if the leishmaniosis clinical symptoms do not return after drug treatment (post-drug treatment re-exposure to the parasites notwithstanding). Moreover, the mouse model does not faithfully recapitulate canine *Leishmania* infection. For example, mice show no clinical signs and do not die from parasite, whereas dogs do. Thus, a skilled person cannot, with any certainty, expect that a treatment method capable of reducing the number of *L. donovani* parasites in mice, will also prevent clinical signs and death—caused by *L. infantum*—in a dog. Adding to the uncertainty is that *Leishmania* parasites are notoriously resistant to drug treatment, and many drugs useful in combating other diseases (including diseases caused by related protozoans) are not efficacious against *Leishmania*. For example, *Leishmania* parasites are well-known to reduce drug concentration by both decreasing drug uptake and by increasing drug efflux/sequestration (Haldar, 2011). Finally, anti-leishmaniosis drugs are extremely toxic, and thus poorly tolerated by humans and non-human animals alike.

Thus, there remains a need for effective and efficient methods of eradicating or curing *leishmania* infections.

REFERENCES

Baneth, G et al. "Canine leishmaniosis—new concepts and insights on an expanding zoonosis: part one." Trends in Parasitology Vol. 24, No. 7, pgs 324-30.

Dantas-Torres, F et al. "Canine leishmaniosis in the Old and New Worlds: unveiled similarities and differences." Trends in Parasitology December 2012, Vol. 28, No. 12, pgs 531-38.

Gradoni L. et al., 2005, "Failure of a multi-subunit recombinant leishmanial vaccine (MML) to protect dogs from *Leishmania infantum* infection and to prevent disease progression in infected animals." Vaccine 23:5245-51.

Grosjean N L et al., 2003, "Disputes prevalence of *Leishmania* carriers in the United States—Response." J Am Vet Med Assoc. 222:603-606.

Haldar et al., 2011, "Use of Antimony in the Treatment of Leishmaniosis: Current Status and Future Directions." Molecular Biology International. 2011.

Lindsay D S et al., 2002, Compend Cont Educ Pract Vet 24:304-312.

McConkey S E et al., 2002, Canine Vet J 43:607-609.

Manna, L. et al. "Real-time PCR assay in *Leishmania*-infected dogs treated with meglumine antimoniate and allopurinol." The Veterinary Journal 177 (2008) 279-282.

Maroli M. et al., 2001, Med. Vet. Entomol. 15:358-63.

Martínez-Subiela S et al., 2002, "Serum concentrations of acute phase proteins in dogs with leishmaniosis." Vet Rec 150:241-244.

Mateo M. et al. "Comparative study on the short term efficacy and adverse effects of miltefosine and meglumine antimoniate in dogs with natural leishmaniosis." Parasitol Res. 2009 July; 105(1):155-62.

Mazloumi Gavgani A. S. et al., 2002, Lancet 360:374-9.

Miró, G. et al. "Current situation of *Leishmania infantum* infection in shelter dogs in northern Spain." Parasites & Vectors 2012, 5:60, pgs 1-7.

Moreira Jr. E. D. et al., 2004, Vet. Parasitol. 122:245-52.

Oliva, G. et al. "Guidelines for treatment of leishmaniosis in dogs." JAVMA, Vol 236, No. 11, Jun. 1, 2010.

Petersen C A. "Leishmaniosis, an Emerging Disease Found in Companion Animals in the United States." Topics in Companion Animal Med. Vol. 24, No. 4, November 2009.

Ready, P D. "Leishmaniosis emergence in Europe." Euro Surveill. 2010; 15(10):pii=19505.

Solano-Gallego, L. et al. "LeishVet guidelines for the practical management of canine leishmaniosis." Parasites & Vectors 2011, 4:86, pgs 1-16.

Wyllie S et al. "The Anti-Trypanosome Drug Fexinidazole Shows Potential for Treating Visceral Leishmaniosis." Sci Transl. Med 4, 119, 2012.

SUMMARY OF THE INVENTION

The present invention demonstrated for the first time that fexinidazole treatment can substantially or completely eliminate or cure *L. infantum* infection in canines. No relapse was observed 180 days after treatment initiation. Methods of the invention include methods for treating animals with fexinidazole to eliminate or cure, substantially or completely, infections caused by *Leishmania* parasites. As used herein, the terms "eliminate" and "eradicate" should be considered to have synonymous meanings.

Veterinary compositions of the invention may be in the form of soft chewable formulations that are palatable for animals, or any other suitable dosage form. For example, the formulation may be a tablet, a paste, a feed premix, a powder, or a gel. In other embodiments, the compositions of the invention may include one or more additional active agents.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

This disclosure contains no figures or drawings.

DETAILED DESCRIPTION OF THE INVENTION

The present invention provides novel and non-obvious methods for curing animals suffering from infection by *Leishmania* parasites. The methods generally comprise administering to an animal in need thereof effective amounts of fexinidazole for a period of time sufficient to eliminate or cure, completely or substantially, the *Leishmania* infection.

As used herein, "completely curing" and "completely eliminating/eradicating" (and respective grammatical variants thereof) are synonymous expressions, which mean that a given treatment regimen has eliminated >99% to 100% of the infecting *Leishmania* parasites, and that the clinical signs owing to the *Leishmania* parasites do not return. A canine "completely cured" of *Leishmania* infection is able to recover completely after fexinidazole treatment, with no sign of relapse, notwithstanding re-exposure to *Leishmania* parasites subsequent to the treatment regimen.

As used herein, "substantially curing" and "substantially eradicating" (and respective grammatical variants thereof) are synonymous expressions, which mean that a given treatment regimen has eliminated between about 85% to up to 99% of the infecting *Leishmania* parasites, and that the clinical signs owing to the *Leishmania* parasites do not return, or are minor. A canine "substantially cured" of *Leishmania* infection may also recover completely, notwithstanding re-exposure to *Leishmania* parasites subsequent to the treatment regimen.

In various embodiments, sufficient amounts of fexinidazole are administered to canines, to eliminate sufficient amounts of *Leishmania* parasites, such that there are no remaining parasites, or if there are, the canine's immune system is able to clear the remaining *Leishmania* parasites, to allow complete recovery. In an embodiment, no clinical signs nor detectable levels of parasites remain after an elimination- or curing-sufficient fexinidazole treatment regimen. In a particular embodiment, no clinical signs, nor detectable levels of parasites, are observed for at least about 30, 40, 50, 60, 70, 80, 90, 100, 110, 120, 130, 140, 150, 160, 170, or 180 days following the treatment regimen. In an embodiment, the canine remains completely parasite-free for at least one year following the treatment regimen, provided that the canine is not re-exposed (during that one year) to infecting amounts of Leishmania parasites.

In one embodiment of the method, sufficient amounts of fexinidazole are administered according to a sufficient dosing regimen, to produce in the canines fexinidazole plasma levels that are sufficient to eliminate or cure, substantially or completely, the Leishmania infections. In a particular embodiment, the plasma levels are sufficient to completely eliminate or cure the infections.

In a particular embodiment, the sufficient fexinidazole plasma levels are achieved by administering oral veterinary compositions comprising an effective amount of fexinidazole over a period of time of at least about twenty days. The fexinidazole may be administered according to any effective regimen, including, but not solely, once weekly, twice weekly, once daily, or twice daily. All that is required is that dosing regimen maintains a sufficient fexinidazole plasma level, over a sufficient period of time, to substantially or completely eliminate or cure the Leishmania infections. In multiple dosing studies, it was shown that fexinidazole, given orally to dogs at doses of 50, 200 and 800 mg/kg/day, for 28 consecutive days, was well tolerated.

As used herein, the following abbreviations have the following definitions: "AUC0-24"=Area under the plasma concentration vs. time curve up to 24 hours post dosing; "AUC0-t(last)"=Area under the plasma concentration vs. time curve up to finite time; "Cmax"=Maximal plasma concentration; "CV"=Coefficient of variation of the mean; "LLOQ"=Lower limit of quantification; "MS"=Mass-spectrometry; "QC"=Quality control sample; "$R^2$"=Correlation coefficient; "$R_A$"=Accumulation ratio; "SD"=Standard deviation of the mean; "STD"=Standard sample; "$t_{1/2, z}$"=Terminal half-life; "$t_{max}$"=Time to peak plasma concentration; and "ULOQ"=Upper limit of quantification.

In an embodiment, the fexinidazole may be administered to the canine as an aqueous oral suspension, comprising 5% TWEEN 80 and 0.5% Methyl cellulose 400 cP (METHOCEL). Provided in this format, fexinidazole suspensions of 5, 20, and 80 mg fexinidazole/mL may be prepared such that 10 mL of each concentration contains 50, 200, and 800 mg fexinidazole, respectively.

Moreover, fexinidazole was extensively metabolized to the sulfone and sulfoxide derivatives both after single and repeated administration. Since only minor effects were observed at the 800 mg/kg/day dose, and no effects were observed at the 200 mg/kg/day dose, inventers envision that the actual minimum no observable effects level (NOEL) may lie somewhere between 200 and 800 mg/kg/day. Moreover, inventors expect that a wide variety of dosing regimens are now available to the skilled person to achieve the necessary and sufficient fexinidazole plasma levels. For example, and as further outlined in the Examples below, any dosing regimen that produces substantially similar fexinidazole plasma levels, as compared to those levels produced by giving the dogs about 60 mg/kg/day for about twenty-eight days, is expected to substantially or completely eliminate the Leishmania parasites. Table 1 presents the systemic fexinidazole exposure following dosing of dogs with 50, 200, and 800 mg/kg/day.

TABLE 1

Mean ± SD systemic exposure to fexinidazole

| | | Male Dog | | | Female Dog | | |
|---|---|---|---|---|---|---|---|
| Dose (mg/kg/day) | Day | Cmax (ng/mL) | tmax (hour) | AUC0-t (last) (ng · hour/mL) | Cmax (ng/mL) | tmax (hour) | AUC0-t (last) (ng · hour/mL) |
| 50 (n = 3) | D1 | 31.2 ± 12.4 | 0.5 ± 0 | 140 ± 147 | 42.4 ± 10.6 | 1 ± 0.87 | 237 ± 105 |
| | D14 | 26.5 ± 13 | 0.5 ± 0 | 52.1 ± 29.4 | 41.9 ± 2.2 | 1.67 ± 0.58 | 246 ± 117 |
| | D28 | 20.3 ± 7.89 | 1 ± 0 | 124 ± 67 | 36.3 ± 15.1 | 1 ± 0 | 87.1 ± 38.1 |
| 200 (n = 3) | D1 | 54.9 ± 10.8 | 1 ± 0.87 | 419 ± 61.4 | 84.1 ± 36.7 | 1 ± 0 | 454 ± 119 |
| | D14 | 78.1 ± 23.5 | 1 ± 0.87 | 452 ± 41.1 | 77.7 ± 50.8 | 2 ± 0 | 443 ± 217 |
| | D28 | 57.9 ± 12.5 | 1 ± 0 | 395 ± 15.8 | 73 ± 12 | 1 ± 0 | 377 ± 83.5 |
| 800 (n = 5) | D1 | 100 ± 21.2 | 1.1 ± 0.55 | 776 ± 182 | 184 ± 75.6 | 1.2 ± 0.45 | 895 ± 437 |
| | D14 | 128 ± 56.9 | 1 ± 0 | 929 ± 268 | 152 ± 44 | 1.4 ± 0.55 | 1170 ± 309 |
| | D28 | 86.2 ± 38.5 | 1.2 ± 0.4 | 736 ± 141 | 101 ± 47.1 | 1 ± 0 | 956 ± 378 |

TABLE 2

Mean ± SD systemic exposure to the sulfone metabolite

| | | Male | | | Female | | |
|---|---|---|---|---|---|---|---|
| Dose (mg/kg/day) | | Cmax (µg/mL) | tmax (hour) | AUC0-t (last) (µg-hour/mL) | Cmax (µg/mL) | tmax (hour) | AUC0-t (last) (µg-hour/mL) |
| 50 (n = 3) | D1 | 7.17 ± 1.74 | 8 ± 0 | 126 ± 28.1 | 10 ± 1.6 | 6.67 ± 2.31 | 170 ± 37.8 |
| | D14 | 5.57 ± 2.19 | 4 ± 0 | 78 ± 35.3 | 9.98 ± 1.25 | 6.67 ± 2.31 | 173 ± 26.9 |
| | D28 | 7.11 ± 1.21 | 8 ± 0 | 121 ± 19.1 | 6.79 ± 0.56 | 3.33 ± 1.15 | 107 ± 22.5 |
| 200 (n = 3) | D1 | 17.2 ± 1.69 | 13.3 ± 9.24 | 338 ± 50.8 | 18.1 ± 3.42 | 12 ± 10.6 | 358 ± 85.7 |
| | D14 | 22 ± 5.59 | 5.33 ± 2.31 | 387 ± 49.5 | 21.5 ± 2.42 | 5.33 ± 2.31 | 381 ± 61.2 |
| | D28 | 14 ± 3.31 | 4 ± 4 | 258 ± 48 | 15.4 ± 2.66 | 11.7 ± 10.1 | 277 ± 29.9 |

TABLE 2-continued

Mean ± SD systemic exposure to the sulfone metabolite

| Dose (mg/kg/day) | | Male | | | Female | | |
|---|---|---|---|---|---|---|---|
| | | Cmax (μg/mL) | tmax (hour) | AUC0-t (last) (μg-hour/mL) | Cmax (μg/mL) | tmax (hour) | AUC0-t (last) (μg-hour/mL) |
| 800 (n = 5) | D1 | 38.6 ± 2.83 | 17.6 ± 8.76 | 705 ± 94.9 | 33.6 ± 10.9 | 11.2 ± 7.16 | 614 ± 216 |
| | D14 | 34.6 ± 7.42 | 5.6 ± 2.19 | 640 ± 163 | 38.6 ± 4.73 | 8 ± 0 | 667 ± 67.8 |
| | D28 | 20.8 ± 4.14 | 12.4 ± 9.81 | 388 ± 68.2[1] 601 ± 29[2] | 26 ± 7.7 | 7.2 ± 1.79 | 477 ± 145[1] 693 ± 351[2] |

[1]AUC0-24;
[2]n = 2

TABLE 3

Mean ± SD systemic exposure to the sulfoxide metabolite

| Dose (mg/kg/day) | | Male | | | Female | | |
|---|---|---|---|---|---|---|---|
| | | Cmax (μg/mL) | tmax (hour) | AUC0-t (last) (μg · hour/mL) | Cmax (μg/mL) | tmax (hour) | AUC0-t (last) (μg · hour/mL) |
| 50 (n = 3) | D1 | 3.55 ± 1.3 | 1 ± 0 | 19.2 ± 5.82 | 3.97 ± 0.74 | 1.33 ± 0.58 | 20 ± 6.81 |
| | D14 | 2.24 ± 0.45 | 1 ± 0 | 8.51 ± 2.53 | 3.73 ± 0.73 | 1.6 7 ± 0.58 | 18.8 ± 2.06 |
| | D28 | 1.83 ± 0.57 | 1.67 ± 0.58 | 14.2 ± 2.72 | 2.72 ± 0.73 | 1 ± 0 | 9.88 ± 2.72 |
| 200 (n = 3) | D1 | 7.55 ± 1.03 | 1.67 ± 0.58 | 50.7 ± 8.61 | 8.7 ± 3.95 | 0.83 ± 0.29 | 52.1 ± 20.6 |
| | D14 | 8.96 ± 2.53 | 2 ± 0 | 56.1 ± 9.96 | 9.02 ± 3.69 | 2 ± 0 | 57.2 ± 24.3 |
| | D28 | 5.76 ± 1.17 | 1.33 ± 0.58 | 42.2 ± 6.46 | 5.43 ± 0.34 | 1 ± 0 | 33.8 ± 1.65 |
| 800 (n = 5) | D1 | 13.4 ± 3.22 | 1.5 ± 0.71 | 104 ± 11.3 | 15.6 ± 4.64 | 1.6 ± 0.55 | 121 ± 44.4 |
| | D14 | 12.5 ± 2.85 | 1.2 ± 0.45 | 113 ± 39.9 | 14.8 ± 5.1 | 2 ± 1.22 | 144 ± 37.1 |
| | D28 | 9.35 ± 3.55 | 1.6 ± 0.55 | 74.3 ± 14.4[1] 121 ± 33[2] | 9.48 ± 3.38 | 1.4 ± 0.55 | 89 ± 45.2 |

[1]AUC0-24;
[2]n = 2

TABLE 4

Average plasma concentrations (ng/mL) of fexinidazole after single (D1) and repeated (D14 and D28) oral administrations of fexinidazole at a dose of 50 and 200 mg/kg/day.

| | Dose (mg/kg/d) | |
|---|---|---|
| | 50 | 200 |
| Hours | [Fexinidazole Plasma] (ng/mL) | |
| Day 1 | | |
| 0 | <5 | <5 |
| 0.5 | 34.5 | 52.1 |
| 1 | 30.3 | 61.3 |
| 2 | 23.8 | 45.9 |
| 4 | 12.6 | 22.6 |
| 8 | <5 | 9.9 |
| 24 | <5 | 13.0 |
| Day 14 | | |
| 0 | <5 | 16.6 |
| 0.5 | 28.8 | 53.4 |
| 1 | 29.5 | 63.2 |
| 2 | 26.8 | 70.2 |
| 4 | ~9 | 27.6 |
| 8 | <5 | 13.5 |
| 24 | <5 | 10.2 |
| Day 28 | | |
| 0 | <5 | <5 |
| 1 | 28.3 | 65.4 |
| 2 | 17.5 | 44.6 |
| 4 | 14.3 | 23.5 |
| 8 | ~5 | 12.4 |
| 24 | <5 | 12.4 |

Using the herein disclosed data and methods, a skilled person can modify the fexinidazole dosing regimen, with only the exertion of routine optimization, to achieve fexinidazole plasma levels sufficient to substantially or completely cure canines of *leishmania* parasites. As further detailed in the Examples below, an oral fexinidazole dose of 60 mg/kg/day, for 28 days, was sufficient to cure canines of *leishmania* parasites. Thus, in an embodiment, the *leishmania*-curing method comprises administering to a *leishmania* parasite-infected canine a sufficient amount of fexinidazole such that, on any given day during treatment, the fexinidazole plasma concentration exceeds about 10 ng/mL to about 30 ng/mL for at least about 1 hour during said day. In a particular embodiment, the fexinidazole plasma concentration exceeds about 10 ng/mL to about 30 ng/mL for at least about 2 hours during said day. In another embodiment, the plasma concentration is measured to be greater than about 30 ng/mL to greater than about 60 ng/mL for at least 1 time point during said day.

In another embodiment, treatment for twenty-eight days may be used to substantially or completely eliminate the parasites, thus substantially or completely curing the canines of the infecting parasites. In a particular embodiment, administering 60 mg/kg/day to a *leishmania*-infected canine is sufficient to substantially or completely cure the canine of the infection. In a more particular embodiment, the canine is completely cured.

In yet another embodiment, a complete parasite-curing amount of fexinidazole is about 70, 80, 90, 100, 110, 120, 130, 140, 150, 160, 170, 180, 190, or 200 mg/kg/day.

The oral veterinary compositions of the invention include, but are not limited to, soft chewable and chewable tablet compositions. The invention includes at least the following features:

(a) palatable oral veterinary compositions, including soft chewable and chewable tablet compositions, that provide superior and surprising efficacy against *Leishmania* parasites comprising an effective amount, including a substantially-curing amount, or a completely-curing amount, of at least fexinidazole together with a pharmaceutically acceptable carrier or diluent;

(b) methods for the treatment and/or prevention of parasitic infections and infestations in an animal comprising administering an effective amount of an oral veterinary composition comprising at least fexinidazole together with a pharmaceutically acceptable carrier or diluent;

(c) use of oral veterinary compositions comprising at least fexinidazole, together with a pharmaceutically acceptable carrier or diluent in the prevention or treatment of animal parasites.

(d) methods for the treatment and/or prevention of parasitic infections and infestations in an animal comprising administering an effective amount of a composition comprising at least fexinidazole, together with a pharmaceutically acceptable carrier or diluent;

(e) use of oral veterinary compositions comprising at least fexinidazole, together with a pharmaceutically acceptable carrier or diluent in the treatment and/or prevention of a parasitic infestation and infections in an animal;

(f) a chewable oral composition comprising fexinidazole for use in the treatment or prophylaxis of a parasitic infection or infestation in an animal; and (g) the use of fexinidazole in the preparation of a chewable oral veterinary composition for the treatment, cure, and/or elimination, substantial or complete, of a parasitic infection or infestation in an animal.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), swine (e.g., pig), ovine (e.g., sheep, goats, lamas, bisons), avian (e.g., chicken, duck, goose, turkey, quail, pheasant, parrot, finches, hawk, crow, ostrich, emu and cassowary), fish (e.g. tilapia, catfish, trout, salmon, bass, carp, shellfish, tuna, cod), primate (e.g., prosimian, tarsier, monkey, gibbon, ape), and humans. The term "animal" also includes an individual animal in all stages of development, including embryonic and fetal stages.

By "treating" or "treat" or "treatment" is intended the application or administration of a composition of the invention to an animal that has a parasitic infestation for the curing (elimination) of the parasite or the reduction of the number of the parasites infesting the animal undergoing treatment. Moreover, the cure may be substantial or complete, and it is noted that the compositions of the invention may also be used to prevent such a parasitic infestation.

The compositions of the invention are administered in parasiticidally effective amounts which are suitable to control the parasite in question to the desired extent, including substantially or completely eradicating/eliminating or curing, and as described below. In each aspect of the invention, the compounds and compositions of the invention can be applied against a single pest or combinations thereof. The expression "effective amount," as used herein, means a concentration of the active agent in the composition sufficient to elicit the desired biological response against the target parasite(s) after administration of the composition to the animal, as measured by methods known in the art and/or described in the Examples herein. The effective amount may result in substantial or complete cure of the parasitic infection.

In some embodiments, an "effective amount" of the active agent in the composition will provide an efficacy of at least 70% against the target parasite compared to an untreated control. In other embodiments, "an effective amount" of the active agent may provide an efficacy of at least 80%, or at least 85% compared to untreated controls. More typically, "an effective amount" of the active agent will provide an efficacy of at least 90%, at least 93%, at least 95% or at least 97% against the target parasite. In certain embodiments, including the treatment of *Leishmania* infection, the term "effective amount" will provide an efficacy of between 99 and 100%.

More specifically, and consistent with the above-recited definitions, a "substantially eradicating/curing effective amount" thus means an "effective amount" sufficient to "substantially eliminate" the parasitic infection (i.e. 85% to 99% elimination or cure). Similarly, a "completely eradicating/curing effective amount" thus means an "effective amount" sufficient to "completely eliminate/cure" the parasitic infection (i.e. 99% to 100% elimination/cure).

As used herein the term "palatable" means an oral veterinary composition that is readily accepted by canines, including dogs, without any coaxing or with some coaxing. Palatable compositions are compositions that score at least 2 using a palatability assessment method wherein dog owners score the composition from 0 to 3, wherein dogs scoring 0 do not consume the composition; dogs scoring 1 consume the composition after some time; dogs scoring 2 consume the composition with some coaxing and dogs scoring 3 consume the composition readily. A skilled person is well-versed in these palatability standards and scoring regimes.

In an embodiment, the fexinidazole is supplied as tablets, including palatable tablets. Infected dogs may be given 60 mg/kg/day of fexinidazole over twenty-eight days to treat *Leishmania* infections. In another embodiment, treating dogs for twenty-eight days completely cures infection by *Leishmania* parasites. In a particular embodiment, there is no relapse for at least 180 days following the treatment regimen.

In another embodiment, the daily dose for dogs may be around 100 mg/kg. The tablets may contain, for example, 500 mg of fexinidazole. In such a case, one 500 mg tablet would treat a 10 kg dog. The tablet may also be scored to accommodate intermediate size dogs.

Now that the instant disclosure has been provided, persons skilled in the art will immediately understand that the parasite-curing levels of fexinidazole may be achieved (in the affected canine) by any reasonable means. For example, the fexinidazole may be provided not only as a tablet, but by any other suitable dosage form. In an embodiment, the fexinidazole may be administered orally, topically, parenterally, subcutaneously, transdermally, or any other reasonable administration means. In another embodiment, the fexinidazole may be provided as a suspension, a slurry, a capsule, a tablet, a soft chew, a paste, a gel, a topical solution, or any other suitable dosage form.

Additional Active Agents

In one embodiment, the invention provides a chewable (including soft-chewable) veterinary composition comprising at least fexinidazole and at least one other active ingredient, formulated with a pharmaceutically acceptable carrier or diluent. Particularly useful chewable formulations are disclosed in US 20130203692 A1, which is herein incorporated by reference in its entirety.

In some embodiments, the additional active agents may include, but are not limited to, acaricides, anthelmintics, anti-parasitics and insecticides. Anti-parasitic agents can include both ectoparasiticidal and/or endoparasiticidal agents.

Veterinary pharmaceutical agents that may be included in the compositions of the invention are well-known in the art (see e.g. Plumb' Veterinary Drug Handbook, 5th Edition, ed. Donald C. Plumb, Blackwell Publishing, (2005) or The Merck Veterinary Manual, 9th Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, afoxolaner, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide +/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, clonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles, are known in the art and are suitable for combination with the isoxazoline compounds in the oral compositions of the invention. Examples of such arylpyrazole compounds include but are not limited to those described in U.S. Pat. Nos. 6,001,384; 6,010,710; 6,083,519; 6,096,329; 6,174,540; 6,685,954, 6,998,131 and 7,759,381 (all of which are incorporated herein by reference). A particularly preferred arylpyrazole active agent is fipronil.

In another embodiment of the invention, one or more macrocyclic lactones or lactams, which act as an acaricide, anthelmintic agent and/or insecticide, can be included in the compositions of the invention.

The macrocyclic lactones that may be used in the compositions of the invention include, but are not limited to, the naturally produced avermectins (e.g. including the components designated as A1a, A1b, A2a, A2b, B1a, B1b, B2a and B2b) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin A3, milbemycin A4, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schöonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12th ed., S. Budavari, Ed., Merck & Co., Inc. Whitehouse Station, N.J. (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

The invention will now be further described by way of the following non-limiting examples.

EXAMPLES

Toxicology summary. In mice and rats, the maximum fexinidazole (FEX) dose after oral administration is 10 g/kg of body weight. Toxicology studies were completed in beagles with daily doses up to 125 mg/kg/day for 90 days (13 weeks) with no observed adverse events (AEs). Reproductive toxicity studies indicated no embryotoxic effects for rats or rabbits following oral administration of 200 mg/kg for 10 days and 40 mg/kg, for 13 days respectively. Further, the mammalian cell mutagenicity on a bone marrow micronucleus study was negative at all test concentrations (500, 1000 and 2000 mg/kg), and FEX does not induce chromosome damage in vitro or in vivo. Finally, as regards PK, labeled FEX and its metabolites were excreted within 3 days in the feces (52-58%) and urine (36-40%). The main metabolites are the sulfoxide, the sulfone, and the corresponding phenolic fragments. The sulfoxide and sulfone were active against *Leishmania donovani* amastigotes grown in macrophages, whereas the parent compound (FEX) was inactive (Wyllie S et al., 2012).

Example 1

Efficacy of Fexinidazole in Dogs Infected with *L. infantum*

In a clinical study, dogs infected with *L. infantum* were treated with meglumine antimoniate (GLUCANTIME®, Merial) as a positive control, or FEX (Table 5). Eight blocks of two animals were formed based antibody titers and biological scores. Six dogs in each group were naturally infected by housing them in an endemic area for two years and two dogs in each group were artificially infected by intravenous administration of a known quantity of parasites recovered from the spleen of an infected dog.

The first group (FEX) was compared to the second group, which was treated with 27 mg/kg GLUCANTIME (meglumine antimoniate, or 100 mg/kg of dNMA) "GLU"), over 28 days.

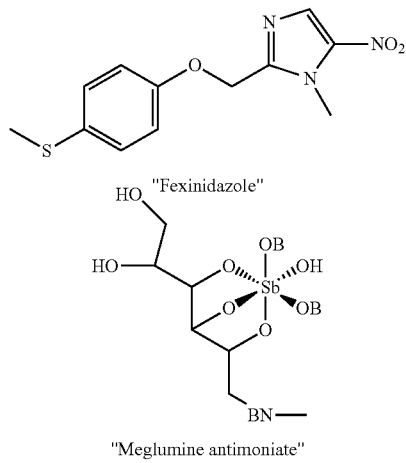

"Fexinidazole"

"Meglumine antimoniate"

Variables. The Clinical Score is an additive score of various clinical signs (body condition, lymphadenopathy, splenomegaly, appetite, behavior, mucous membrane color, dermatopathology, ocular signs, digestive signs, arthropathy) evaluated before treatment and on Days 7, 14, 21, 28, 57, 184, 219, 254, 282, 310, 345, 400 and 436. The Overall Biological Score is an additive score based on the severity of changes in hematology/chemistry values (creatinine, urine protein/creatinine, Hct, globulin, ALAT), evaluated pretreatment and on Days 28, 57, and 181. The *L. infantum* immunofluorescent antibody titers (IFAT) were determined from samples collected before treatment and on Days 28, 57, and 181. Finally, quantitative PCR (qPCR) for *L. infantum* was conducted on spleen aspirates collected before treatment and on Days 28, 57, 142, 184, and 373.

TABLE 5

Study details.

| Group | Active | Dose | Route | Day | Total No. Animals |
|---|---|---|---|---|---|
| 1 | Glucantime | 100 mg/kg of dNMA once daily | SC | 0-27 | 8 |
| 2 | Fexinidazole | 60 mg/kg once daily | PO | 0-27 | 8 |

TABLE 6

Clinical scores.

| | | Clinical Scores on Day | | | | | | | | | | | | |
|---|---|---|---|---|---|---|---|---|---|---|---|---|---|---|
| Group | Block | −7 | 7 | 14 | 21 | 28 | 57 | 184 | 219 | 254 | 282 | 310 | 345 | 400 | 436 |
| 1 | 1 | 0 | 0 | 0 | 0 | 0 | 0 | 0 | 0 | 0 | 0 | 0 | 0 | 0 | 0 |
| 1 | 2 | 2 | 0 | 2 | 3 | 0 | 0 | 0 | — | — | — | — | — | — | — |
| 1 | 3 | 3 | 7 | 7 | 9[1] | — | — | — | — | — | — | — | — | — | — |
| 1 | 4 | 2 | 1 | 0 | 1 | 0 | 0 | 0 | — | — | — | — | — | — | — |
| 1 | 5 | 2 | 2 | 0 | 0 | 0 | 0 | 0 | 0 | 3 | 3 | 2 | 0 | 1 | 4 |
| 1 | 6 | 0 | 0 | 0 | 0 | 0 | 0 | 0 | 0 | 0 | 0 | 0 | 0 | 0 | 0 |
| 1 | 7 | 0 | 0 | 0 | 2 | 0 | 0 | 0 | — | — | — | — | — | — | — |
| 1 | 8 | 0 | 0 | 0 | —[2] | — | — | — | — | — | — | — | — | — | — |
| 2 | 1 | 6 | 4 | 2 | 0 | 0 | 2 | 0 | 0 | 0 | 0 | 0 | 0 | 0 | 0 |
| 2 | 2 | 0 | 2 | 0 | 0 | 0 | 0 | 0 | 0 | 0 | 0 | 0 | 0 | 0 | 1 |
| 2 | 3 | 4 | 6 | 3 | 0 | 1 | 0 | 0 | 1 | 4 | 2 | 2 | 2 | 1 | 0 |
| 2 | 4 | 6 | 6 | 3 | 2 | 2 | 2 | 0 | 0 | 0 | 0 | 0 | 0 | 2 | 2 |
| 2 | 5 | 0 | 1 | 2 | 0 | 0 | 2 | 0 | 0 | 0 | 0 | 0 | 0 | 0 | 0 |
| 2 | 6 | 3 | 3 | 3 | 2 | 1 | 0 | 0 | 0 | 0 | 0 | 0 | 0 | 0 | 0 |
| 2 | 7 | 0 | 0 | 0 | 0 | 0 | 0 | 0 | 0 | 0 | 0 | 0 | 0 | 0 | 0 |
| 2 | 8 | 0 | 0 | 0 | 0 | 0 | 0 | 1 | 0 | 0 | 0 | 0 | 0 | 0 | 0 |
| Ave | Gp 1 | 1.1 | 1.3 | 1.1 | 2.1 | 1.33 | 1.33 | 0.0 | 0.0 | 1.0 | 1.0 | 0.7 | 0.0 | 0.3 | 1.3 |
| | Gp 2 | 2.4 | 2.8 | 1.6 | 0.5 | 0.5 | 0.8 | 0.1 | 0.1 | 0.5 | 0.3 | 0.3 | 0.3 | 0.4 | 0.4 |

[1] Dog Group 1 Block 3 removed on Day 28 due to continued deterioration
[2] Dog Group 1 Block 8 removed on Day 20 due to GLUCANTIME toxicity
[3] Dogs Group 1 Blocks 2, 4, 7 removed after Day 184 due to lack of GLUCANTIME efficacy
[3] Treatment Group 1 D28 & D57 include D21 data from the Group 1, Block 3 dog, carried forward

TABLE 7

Overall Biological scores.

| Treatment Group | Block | Day −14 | Day 28 | Day 57 | Day 181 |
|---|---|---|---|---|---|
| 1 | 1 | 3 | 2 | 1 | 0 |
| 1 | 2 | 7 | 3 | 1 | 6 |
| 1 | 3 | 2 | $2^1$ | — | — |
| 1 | 4 | 2 | 3 | 1 | 2 |
| 1 | 5 | 6 | 2 | 1 | 3 |
| 1 | 6 | 1 | 1 | 4 | 3 |
| 1 | 7 | 1 | 4 | 4 | 2 |
| 1 | 8 | 3 | $5^2$ | — | — |
| 2 | 1 | 4 | 3 | 2 | 0 |
| 2 | 2 | 7 | 2 | 0 | 1 |
| 2 | 3 | 5 | 1 | 2 | 0 |
| 2 | 4 | 2 | 1 | 2 | 0 |
| 2 | 5 | 5 | 2 | 3 | 0 |
| 2 | 6 | 3 | 3 | 3 | 3 |
| 2 | 7 | 1 | 0 | 0 | 0 |
| 2 | 8 | 0 | 0 | 0 | 1 |
| Average | Group 1 | 3.1 | 2.4 | $2.0^3$ | 2.7 |
|  | Group 2 | 3.4 | 1.5 | 1.5 | 0.6 |

[1]Animal in Group 1 Block 3 removed on D28 due to continued deterioration
[2]Animal in Group 1 Block 8 (Group 1 Block 8) removed on D20 due to GLUCANTIME toxicity Score calculated from samples collected on D16
[3]Treatment Group 1 D57 and D181 include D28 data from the Group 1 Block 3 dog, carried forward

TABLE 8

L. infantum IFAT Antibody titers

| Treatment Group | Block | −14 | 28 | 57 | 181 |
|---|---|---|---|---|---|
| 1 | 1 | >1/10 240 | 1/10 240 | 1/1 280 | 1/1.280 |
| 1 | 2 | 1/10 240 | 1/5 120 | 1/1 280 | 1/10.240 |
| 1 | 3 | 1/10 240 | 1/2 $560^1$ | — | — |
| 1 | 4 | 1/10 240 | 1/2 560 | 1/1 280 | 1/5.120 |
| 1 | 5 | 1/5 120 | 1/5 120 | 1/2 560 | 1/5.120 |
| 1 | 6 | 1/5 120 | 1/5 120 | 1/1 280 | 1/1.280 |
| 1 | 7 | 1/5 120 | 1/2 560 | 1/1 280 | 1/10.240 |
| 1 | 8 | 1/2 560 | 1/2 $560^2$ | — | — |
| 2 | 1 | >1/10 240 | 1/5 120 | 1/2 560 | 1/5.120 |
| 2 | 2 | 1/10 240 | 1/2 560 | 1/640 | 1/640 |
| 2 | 3 | 1/10 240 | 1/5 120 | 1/1 280 | 1/1.280 |
| 2 | 4 | 1/10 240 | 1/5 120 | 1/1 280 | 1/2.560 |
| 2 | 5 | 1/5 120 | 1/1 280 | 1/640 | 1/640 |
| 2 | 6 | 1/5 120 | 1/5 120 | 1/1 280 | 1/10.240 |
| 2 | 7 | 1/5 120 | 1/1 280 | 1/320 | 1/320 |
| 2 | 8 | 1/5 120 | 1/80 | 1/80 | 1/80 |

[1]Animal removed on D28;
[2]Animal removed on D16. Result obtained from sample collected on Day 16

TABLE 9 qPCR Results

| Treatment Group[1] | Block | qPCR (log copies/mL) on Day | | | | | |
|---|---|---|---|---|---|---|---|
| | | −7 | 28 | 57 | 142 | 184 | 373 |
| 1 | 1 | 5.12 | BLOQ[1] | BLOQ | BLOQ | BLOQ | 3.83 |
| 1 | 2 | 6.87 | 5.77 | 5.14 | 5.57 | 7.01 | —[4] |
| 1 | 3 | 6.17 | $6.40^2$ | — | — | — | — |
| 1 | 4 | 6.70 | 5.81 | 4.78 | 3.94 | 5.62 | —[4] |
| 1 | 5 | 5.81 | 4.04 | BLOQ | BLOQ | BLOQ | BLOQ |
| 1 | 6 | 4.38 | 3.73 | BLOQ | BLOQ | 3.97 | 5.23 |
| 1 | 7 | 6.40 | 5.93 | 4.93 | 4.73 | 5.53 | —[4] |
| 1 | 8 | 5.10 | $5.63^3$ | — | — | — | — |
| 2 | 1 | 7.19 | BLOQ | BLOQ | BLOQ | BLOQ | BLOQ |
| 2 | 2 | 7.11 | BLOQ | BLOQ | BLOQ | BLOQ | BLOQ |
| 2 | 3 | 5.21 | BLOQ | BLOQ | BLOQ | BLOQ | BLOQ |
| 2 | 4 | 5.57 | BLOQ | BLOQ | BLOQ | BLOQ | BLOQ |
| 2 | 5 | 6.58 | BLOQ | BLOQ | BLOQ | BLOQ | BLOQ |
| 2 | 6 | 5.81 | BLOQ | BLOQ | BLOQ | BLOQ | BLOQ |
| 2 | 7 | 6.01 | BLOQ | BLOQ | BLOQ | BLOQ | 3.82 |
| 2 | 8 | BLOQ | BLOQ | BLOQ | BLOQ | BLOQ | BLOQ |

[1]BLOQ = Below Level of Quantification = < log 3.64 copies/mL spleen aspirate
[2]Animal removed on D28;
[3]Animal removed on D16;
[4]Animals removed after D184

Conclusion: The Disclosed *Leishmania* Parasite Curing Method Produced Unexpected Results

*Leishmania* parasite infections have been notoriously challenging to eliminate or cure in animals, including canines. Moreover, *Leishmania* parasites resist the currently available drugs, which are toxic and generally not well-tolerated by the infected animals. Finally, *Leishmania* spp. demonstrate wide variation in their sensitivity and resistance to the various drugs, making it impossible to predict in advance what compounds might effectively eliminate or cure the parasitic infections. Therefore, even though Susan Wyllie had encouragingly shown that fexinidazole was able to suppress infection due to *L. donovani* in mice (Sci Transl. Med 4, 119, 2012), a skilled person could not have predicted the qPCR-confirmed, complete curing efficacy of fexinidazole against a different *Leishmania* parasite (*L. infantum* v. *L. donovani*) in a different animal (canine v. mouse).

* * *

Having thus described in detail preferred embodiments of the present invention, it is to be understood that the invention defined by the above examples is not to be limited to particular details set forth in the above description as many apparent variations thereof are possible without departing from the spirit or scope of the present invention.

What is claimed is:

1. A method for curing a canine animal of a *Leishmania infantum* parasite infection, wherein said canine animal is in need of a cure from the *Leishmania infantum* parasite infection, said method comprising the step of administering fexinidazole to the canine animal in an effective amount, whereby:
   the fexinidazole is metabolized in the canine animal to produce a parasiticidally effective amount of fexinidazole sulfone and sulfoxide metabolites, which are responsible for killing the *Leishmania infantum* parasite; and
   the metabolites are present in the canine animal's plasma in concentrations exceeding 2 ng/mL for at least one hour of each day throughout the fexinidazole administration; and
   wherein the fexinidazole administration is over a course whereby the cured canine animal does not relapse for at least 180 days post fexinidazole administration;
   thereby curing the canine animal.

2. The method of claim 1, wherein the concentration of the fexinidazole metabolites exceeds 10 ng/mL for at least 1 hour during each day of the course of fexinidazole administration.

3. The method of claim 2, wherein the concentration of the fexinidazole metabolites exceeds 30 ng/mL for at least 2 hours during each day of the course of fexinidazole administration.

4. The method of claim 3, wherein, the concentration is measured to be greater than 60 ng/mL for at least 1 time point during each day of the course of fexinidazole administration.

5. The method of claim 1 or 3, wherein the course of fexinidazole administration comprises administering the effective amount of fexinidazole once daily, orally over the course of at least twenty days.

6. The method of claim 1, wherein the course of fexinidazole administration comprises administering the effective amount of fexinidazole once daily for at least twenty-eight days.

7. The method of claim 5, wherein the fexinidazole is micronized and suspended in a solution of and DMSO.

8. The method of claim 3, wherein the course of fexinidazole administration comprises administering the effective amount of fexinidazole once daily for at least twenty-eight days.

9. The method of claim 1, wherein *Leishmania infantum* DNA in the cured animal remains below the level of qPCR detection for at least 180 days post fexinidazole administration.

10. The method of claim 4, wherein the course of fexinidazole administration comprises administering the effective amount of fexinidazole once daily for at least twenty-eight days.

11. The method of claim 3 wherein *Leishmania infantum* DNA in the cured animal remains below the level of qPCR detection for at least 180 days post fexinidazole administration.

12. The method of claim 1, wherein the canine animal does not relapse for at least 365 days post fexinidazole administration.

13. The method of claim 12, wherein *Leishmania infantum* DNA in the cured canine animal remains below the level of qPCR detection for at least 180 days post fexinidazole administration.

* * * * *